US008629284B2

(12) United States Patent
Hueter et al.

(10) Patent No.: US 8,629,284 B2
(45) Date of Patent: *Jan. 14, 2014

(54) CHEMICAL COMPOUNDS

(75) Inventors: Ottmar Franz Hueter, Stein (CH); Peter Renold, Stein (CH); Werner Zambach, Stein (CH); Thomas Pitterna, Stein (CH); Peter Maienfisch, Stein (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 33 days.

This patent is subject to a terminal disclaimer.

(21) Appl. No.: 13/129,063

(22) PCT Filed: Oct. 27, 2009

(86) PCT No.: PCT/EP2009/064102
§ 371 (c)(1),
(2), (4) Date: May 12, 2011

(87) PCT Pub. No.: WO2010/054926
PCT Pub. Date: May 20, 2010

(65) Prior Publication Data
US 2011/0218101 A1    Sep. 8, 2011

(30) Foreign Application Priority Data
Nov. 12, 2008 (GB) .................. 0820710.2

(51) Int. Cl.
A01N 25/26    (2006.01)
A01N 43/80    (2006.01)
C07D 275/06   (2006.01)

(52) U.S. Cl.
USPC ........ 548/212; 548/181; 546/271.1; 514/338; 514/365; 514/373; 504/100; 504/252; 504/269

(58) Field of Classification Search
USPC ........................................ 548/212
See application file for complete search history.

(56) References Cited

U.S. PATENT DOCUMENTS 4,148,798 A * 4/1979 Wade et al. .................... 548/212
4,379,157 A * 4/1983 van Hes et al. ................ 514/373

FOREIGN PATENT DOCUMENTS

| EP | 033984 | 8/1981 |
|---|---|---|
| WO | 2007/057407 | 5/2007 |
| WO | 2007/113119 | 10/2007 |
| WO | 2008/145261 | 12/2008 |

* cited by examiner

*Primary Examiner* — Laura L. Stockton
(74) *Attorney, Agent, or Firm* — R. Kody Jones

(57) ABSTRACT

A compound of the formula I or where W, X and Y are for example each CH; $R^1$ is H; $R^2$ is halogen; and $R^6$ is, for formula I, for example, OH, CN, C3-C8-cycloalkyl, C3-C8-cycloalkyl-C1-C6-alkyl, C2-C6-alkenyl, C2-C6-haloalkenyl, C2-C6-alkenyloxy, C2-C6-alkynyl, C2-C6-haloalkynyl, C2-C6-alkynyloxy, optionally substituted C1 to C3-alkyl, or optionally substituted C1-C6-alkoxy, or $R^6$ is, for formula II, for example, CN, C3-C8-cycloalkyl, or optionally substituted C3-C6-alkyl; and/or salts thereof; and their use as as pesticidal agents.

17 Claims, No Drawings

CHEMICAL COMPOUNDS

This application is a 371 of International Application No. PCT/EP2009/064102 filed Oct. 27, 2009, which claims priority to GB 0820710.2 filed Nov. 12, 2008.

The present invention relates to defined 3-amino-1,2-benzisothiazole dioxide derivatives, and salts thereof, compositions and treated material thereof, and method of using such compounds and salts.

EP 33984, EP 86748, EP 110829, DE 3544436, EP 191734, EP 207891, JP 01319467, JP 02006496, WO 2007057407, WO 2007113119 and WO2008090048 disclose certain 3-amino-1,2-benzisothiazole dioxide derivatives having pesticidal activity.

It has now been found that specific 3-amino-1,2-benzisothiazole dioxide derivatives have pesticidal properties. The present invention, in a first aspect, accordingly relates to a compound of the formula I or II

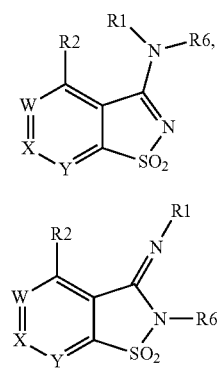

where
W is C—$R^3$;
X is C—$R^4$;
Y is C—$R^5$;
$R^1$ is hydrogen
$R^2$ is halogen;
$R^3$, $R^4$ and $R^5$, independently of each other, are H, halogen, cyano, nitro, C1-C6-alkyl, C1-C6-alkoxy, C1-C6-haloalkyl, C3-C8-cycloalkyl, C2-C6-alkenyl, C2-C6-alkynyl, OD or aryl; where D is C1-C6-alkyl, C1-C6-haloalkyl, C2-C6-alkenyl, C2-C6-alkynyl, C3-C8-cycloalkyl, or aryl; and where the aryl, whenever mentioned, independent of each other, may be unsubstituted, have one or more halogen atoms and/or carry 1, 2 or 3 substituents, independently of one another, selected from the group consisting of cyano, C1-C6-alkyl, C1-C6-haloalkyl, C1-C6-alkoxy and C1-C6-haloalkoxy; and
$R^6$ is, for formula I, OH, CN, C3-C8-cycloalkyl, C3-C8-cycloalkyl-C1-C6-alkyl, C2-C6-alkenyl, C2-C6-haloalkenyl, C2-C6-alkenyloxy, C2-C6-alkynyl, C2-C6-haloalkynyl, C2-C6-alkynyloxy, C1-C3-alkyl, or C1-C6-alkoxy,
wherein the C1-C3-alkyl radical and the C1-C6-alkoxy radical, independent of each other, may be unsubstituted, have one or more halogen atoms and/or may carry 1, 2 or 3 radicals, independently of one another, each selected from the group consisting of cyano, nitro, amino, OH, C1-C6-haloalkyl, C1-C6-alkoxy, C1-C6-haloalkoxy, C1-C6-alkylthio, C1-C6-alkylsulfinyl, C1-C6-alkylsulfonyl, C1-C6-haloalkylthio, (C1-C6-alkoxy)carbonyl, (C1-C6-alkyl)amino, di-(C1-C6-alkyl)amino, C1-C6-alkylcarbonyloxy, arylcarbonyloxy, aryl and heterocyclyl; the aryl group, independent of attachment, may be unsubstituted, have one or more halogen atoms and/or carry 1, 2 or 3 substituents, independently of one another, selected from the group consisting of C1-C6-alkyl, C1-C6-haloalkyl, C1-C6-alkoxy, C1-C6-haloalkoxy, cyano, and nitro; the heterocyclyl group is a 4-7 membered heterocycle, which may be saturated, partially unsaturated or aromatic, which may contain 1, 2, or 3 heteroatom and/or heteroatom group as ring members, independently of one another, selected from C(═O), O, S, and N and may be unsubstituted or substituted with one or two substituents selected from halogen, C1-C6-(halo)alkyl, and C1-C6-(halo)alkoxy; provided that the alkyl radical in the instance it is C2-alkyl is not substituted with a chlorine atom, or
$R^6$ is, for formula II, CN, C3-C8-cycloalkyl, C3-C8-cycloalkyl-C1-C4-alkyl, which may have one or more halogen atoms on the alkyl group and/or cycloalkyl group, C2-C6-alkynyl, C2-C6-haloalkenyl, C2-C6-haloalkynyl, aryl-C1-C4-alkyl, heterocyclyl-C1-C4-alkyl or C3-C6-alkyl, wherein the C3-C6-alkyl radical may be unsubstituted, have one or more halogen atoms and/or may carry 1, 2 or 3 radicals, independently of one another, each selected from the group consisting of cyano, nitro, amino, OH, C1-C6-haloalkyl, C1-C6-alkoxy, C1-C6-haloalkoxy, C1-C6-alkylthio, C1-C6-alkylsulfinyl, C1-C6-alkylsulfonyl, C1-C6-haloalkoxy, C1-C6-haloalkylthio, (C1-C6-alkoxy)carbonyl, (C1-C6-alkyl)amino, di-(C1-C6-alkyl)amino, the aryl group may be unsubstituted, have one or more halogen atoms and/or carry 1, 2 or 3 substituents, independently of one another, selected from the group consisting of C1-C6-alkyl, C1-C6-haloalkyl, C1-C6-alkoxy, C1-C6-haloalkoxy, cyano, and nitro; and the heterocyclyl group is a 4-7 membered saturated, partially unsaturated or aromatic heterocycle which may contain 1, 2, or 3 heteroatom and/or heteroatom group as ring members, independently of one another, selected from C(═O), O, S, and N and may be unsubstituted or substituted with one or two substituents selected from halogen, C1-C6-(halo)alkyl, and C1-C6-(halo)alkoxy;
and/or salts thereof.

The compounds of formula (I) and (II) may exist in different geometric or optical isomers or tautomeric forms. This invention covers all such isomers and tautomers and mixtures thereof in all proportions. In particular, in the case compounds of the formula I or II have one or more centers of chirality, they can be present as mixtures of enantiomers or diastereomers. The present invention provides both the pure enantiomers or di-astereomers or mixtures of each thereof, as well as isotopic forms such as deuterated compounds.

The organic moieties mentioned in the above definitions of the variables are collective terms for individual listings of the individual group members. The prefix Cn-Cm indicates in each case the possible number of carbon atoms in the group. Similarly the terms "x to y membered" indicates the possible number of atoms forming a closed chain in the corresponding ring.

The term halogen denotes in each case fluorine, bromine, chlorine or iodine.

The term "C1-C6-alkyl" as used herein refers to a saturated straight-chain or branched hydrocarbon radical attached via any of the carbon atoms having 1 to 6 carbon atoms, for example, any one of the radicals 1-methylbutyl, 2-methylbutyl, 3-methylbutyl, 2,2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "C1-C6-haloalkyl" as used herein refers to a straight-chain or branched saturated alkyl radical attached via any of the carbon atoms having 1 to 6 carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. According a term "C1-C2-fluoroalkyl" would refer to a C1-C2-alkyl radical which carries 1, 2 ,3, 4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or penta-fluoroethyl.

The term "C1-C6-alkoxy" as used herein refers to a straight-chain or branched saturated alkyl radical having 1 to 6 carbon atoms (as mentioned above) which is attached via an oxygen atom, i.e., for example, any one of methoxy, ethoxy, n-propoxy, 1-methylethoxy, n-butoxy, 1-methylpropoxy, 2-methylpropoxy or 1, 1-dimethylethoxy. Similarly, the terms "alkenoxy", "alkynoxy" and "benzyloxy" refers to the corresponding alkenyl, alkynyl and benzyl radical respectively which is attached via an oxygen atom.

The term "C1-C6-haloalkoxy" as used herein refers to a C1-C6-alkoxy radical as mentioned above which may carry one or more halogen atoms, i.e. fluorine, chlorine, bromine and/or iodine, i.e., for example, any one of chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroeth-oxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy.

The term "(C3-C8-cyloalkyl)thio" as used herein herein refers to a monocyclic hydrocarbon radical having 3 to 8 carbon atoms which is attached via a sulphur atom, for example, 2-cyclopentylthio, 2-cyclopentylthio or 3-cyclobutylthio. Such radicals are also being referred to as (C-C8-cyloalkyl)sulfanyl.

The term "C1-C6-alkylthio" (or C1-C6-alkylsulfanyl : C1-C6-alkyl-S—) as used herein refers to a straight chain or branched saturated alkyl radical having 1 to 6 carbon atoms (as mentioned above) which is attached via a sulfur atom, i.e., for example, any one of methylthio, ethylthio, n-propylthio, 1-methylethylthio, butylthio, 1-methylpropylthio, 2-methylpropylthio or 1,1-dimethylethylthio.

The term "C1-C6-alkylsulfinyl" (or C1-C6-alkyl-S(=O)—) as used herein refers to a straight chain or branched saturated alkyl radical having 1 to 6 carbon atoms (as mentioned above) which is attached via the sulfur atom of the sulfinyl group, i.e., for example, any one of CH3—SO, C2H5—SO, n-propylsulfinyl, 1-methylethyl-sulfinyl, n-butylsulfinyl, 1-methylpropylsulfinyl, 2-methylpropylsulfinyl, 1,1-dimethyl-ethylsulfinyl, n-pentylsulfinyl, 1-methylbutylsulfinyl, 2-methylbutylsulfinyl, 3-methyl-butylsulfinyl, 1,1-dimethylpropylsulfinyl, 1,2-dimethylpropylsulfinyl, 2,2-dimethylpropylsulfinyl or 1-ethylpropylsulfinyl.

The term "C1-C6-alkylsulfonyl" (or C1-C6-alkyl-S(=O)$_2$—) as used herein refers to a straight chain or branched saturated alkyl radical having 1 to 6 carbon atoms (as mentioned above) which is attached via the sulfur atom of the sulfonyl group, i.e., for example, any one of CH3—S02, C2H5—S02, n-propylsulfonyl, (CH3)2CH—S02, n-butylsulfonyl, 1-methylpropylsulfonyl, 2-methylpropylsulfonyl or (CH3)3C-S02. The term "C1-C6-haloalkylthio" as used herein refers to a C1-C6-alkylthio radical as mentioned above which may carry one or more halogen atoms, i.e. chlorine, bromine and/or iodine, i.e., for example, any one of fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio.

The term "C1-C6-alkoxycarbonyl" as used herein refers to a straight chain or branched alkoxy radical having 1 to 6 carbon atoms (as mentioned above) which is attached via the carbon atom of the carbonyl group, i.e., for, any one of methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl.

The term "C2-C6-alkenyl" as used herein refers to a straight chain or branched mono-unsaturated hydrocarbon radical attached via any of the carbon atoms having 2 to 6 carbon atoms and a double bond in any position, i.e., for example, any one of ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1, 1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2, 3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1, 2-trimethyl-2-propenyl, 1-ethyl-1-methyl-2-propenyl, 1-ethyl-2-methyl-1-propenyl or 1-ethyl-2-methyl-2-propenyl.

The term "C2-C6-alkynyl " as used herein refers to a straight chain or branched aliphatic hydrocarbon radical attached via any of the carbon atoms which contains a C—C triple bond and has 2 to 6 carbons atoms: for example, any one of ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "C3-C8-cycloalkyl" as used herein refers to a monocyclic hydrocarbon radical having 3 to 8 carbon atoms, for example, any one of cyclopropyl, cyclobutyl, cyclopentyl, cyclo-hexyl, cycloheptyl or cyclooctyl.

The term "C3-C8-halocycloalkyl" as used herein refers to a monocyclic hydrocarbon radical having 3 to 8 carbon atoms and one or more halogen atoms, such as 2-fluoro-cyclopropyl, 2,2-difluoro-cyclopropyl, 2,2-dichloro-cyclopropyl, 2,2-dibromo-cyclopropyl, 1-fluoro-cyclobutyl, 2-fluoro-cyclobutyl, 3-fluoro-cyclobutyl, 2,2-difluoro-cyclobutyl, 3,3-difluoro-cyclobutyl, 2,2,3,3-tetrafluoro-cyclobutyl, 1-chloro-cyclobutyl, 2-chloro-cyclobutyl, 3-chloro -cyclobutyl, 2,2-dichloro-cyclobutyl, 3,3-dichloro-cyclobutyl, 1-fluoro-cyclopentyl, 3,3-difluoro-cyclopentyl, 3,4-difluoro-cyclopentyl, 1-chloro-cyclopentyl, 2-chloro-cyclopentyl, 3-chloro-cyclopentyl, 3,3-difluoro-cyclohexyl, 1-fluoro-cyclohexyl, 2-fluoro-cyclohexyl, 3-fluoro-cyclohexyl, 4-fluoro-cyclohexyl, 3,3-difluoro-cyclohexyl, 4,4-difluoro-cyclohexyl, 1-chloro-cyclohexyl, 2-chloro-cyclohexyl, 3-chloro-cyclohexyl, 4-chloro-cyclohexyl, 1-fluoro-cycloheptyl, 1-chloro-cycloheptyl, 1-fluoro-cyclooctyl, 1-chloro-cyclooctyl.

The term "(C1-C6-alkyl)amino" as used herein refers to a straight chain or branched saturated alkyl radical having 1 to 6 carbon atoms (as mentioned above) which is attached via the nitrogen atom of the amino group, i.e., for example, any one of methylamino, ethylamino, n-propylamino, 1-methylethylamino, n-butylamino, 1-methylpropylamino, 2-methylpropylamino or 1,2-dimethylethylamino.

The term "di(C1-C6-alkyl)amino" as used herein refers to two straight chain or branched saturated alkyl radicals having 1 to 6 carbon atoms (as mentioned above), each of which is attached via the nitrogen atom of the amino group, for example, any one of N,N-dimethylamino, N,N-diethylamino, N,N-di(1-methylethyl)amino, N,N-dipropylamino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)-amino, N-methyl-N-(2-methypropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethyl-ethyl)amino, N-(1-methylethyl)-N-propylamino, N-butyl-N-propylamino, N-(1-methyl-propyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)-amino, N-(1-methylethyl)-N-(2-methylpropyl)amino, N-(1,1-dimethylethyl)-N-(1-methyl-ethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl) amino, N-(1,1-dimethylethyl)-N-(1-methylpropyl)amino or N-(1,1-dimethylethyl)-N-(2-methylpropyl)-amino.

The term "heterocyclyl" as used herein (and also in heterocyclyl-C1-C6-alkyl) refers to a saturated or partially unsaturated or aromatic cyclic radical having 4 to 7, preferably 5 or 6, ring members, wherein 1, 2 or 3 ring members of the cyclic radical are heteroatoms and/or heteroatom groups, independently, selected from C(=O), O, N and S.

Examples for non-aromatic rings include azetidiyl, pyrrolidinyl, pyrazolinyl, imidazolinyl, pyrrolinyl, pyrazolinyl, imidazol inyl, tetrahydrofuranyl, dihydrofuranyl, 1,3-dioxolanyl, dioxolenyl, thiolanyl, dihydrothienyl, oxazolidinyl, isoxazol idinyl, oxazolinyl, isoxazolinyl, thiazol inyl, isothiazolinyl, thiazolidinyl, isothiazolidinyl, oxathiolanyl, piperidinyl, piperazinyl, pyranyl, dihydropyranyl, tetrahydropyranyl, dioxanyl, thiopyranyl, dihydrothiopyranyl, tetrahydrothiopyranyl, morpholinyl, thiazinyl and the like. Examples for monocyclic 5- or 6-membered heteroaromatic rings include triazinyl, pyrazinyl, pyrimidyl, pyridazinyl, pyridyl, thienyl, furyl, pyrrolyl, pyrazolyl, imidazolyl, triazolyl, tetrazolyl, thiazolyl, oxazolyl, thiadiazolyl, oxadiazolyl, isothiazolyl and isoxazolyl. The heterocyclic group can be substituted. Examples are 2-chloro-pyridinyl-4-yl, 2-chloro-pyridinyl-5-yl, 2-chloro-pyridinyl-6-yl, 2-chlorothiazol-5-yl.

The term "aryl" (and also in aryl-C1-C6-alkyl) as used herein refers to an aromatic hydrocarbon ring, which may be mono-, bi- or tricyclic. Examples of such rings include phenyl, naphthalenyl, anthracenyl, indenyl or phenanthrenyl. A preferred aryl group is phenyl The term "aryl-C1-C6-alkyl" as used herein (and also C3-C8-cycloalkyl-C1-C6-alkyl, heteroaryl-C1-C6-alkyl, heterocyclic-C1-C6-alkyl) refers to the respective radical being bound to the remainder of the molecule via any carbon atoms of the C1-C6-alkylene group. Examples of "aryl-C1-C6-alkyl" are benzyl, 1-phenylethyl and 2-phenylethyl. Similary, for aryl-C2-C6-alkenyl and aryl-C2-C6-alkynyl refers to the aryl radical being bound to the remainder of the molecule via any carbon atoms of the C2-C6-alkenylene and C2-C6 alkynylene group respectively.

The terms, for example, "C2-C6-alkenylthio-C1-C6-alkyl", "C1-C6-alkoxy-C(=O)NR$^x$-C1-C6-alkyl" and "(C3-C8-cyloalkyl)thio-C1-C6-alkyl", whenever present, refer to the corresponding radical attached via any one of the carbon atoms of the C1-C6-alkyl group.

In a preferred embodiment, each C1-C6-moiety, whenever it is indicated, for example, as a C1-C6-alkyl substituent or radical, C1-C6-alkoxy, C1-C6-haloalkoxy, C1-C6-alkylthio, C1-C6-alkylsulfonyl, C1-C6-alkylsulfinyl, C1-C6-haloalkylthio, C1-C6-haloalkyl, (C1-C6-alkyl)amino, di(C1-C6- alkyl)amino, etc, is, independent of the type of moiety (substituent or radical), a C1-C4-moiety, preferably a C1-C3-moiety, for example, any one of a C1-moiety, a C2-moiety or a C3-moiety.

In a preferred embodiment, each C2-C6-moiety, whenever it is indicated, for example, as a C2-C6-alkenyl substituent or radical, C2-C6-alkynyl, C2-C6-haloalkenyl, C2-C6-haloalkynyl, C2-C6-alkenyoxy, C2-C6-alkenyloxy, C2-C6-alkynyloxy, etc, is, independent of the type of moiety, a C2-C5-moiety, preferably a C2-C4-moiety, for example, any one of a C2-moiety, a C3-moiety or a C4-moiety.

In a preferred embodiment, each C3-C8-moiety, whenever it is indicated, for example, as a C3-C8-cycloalkyl substituent or radical, C3-C8-cyclohaloalkyl, C3-C8-cycloalkoxy, etc, is, independent of the type of moiety, a C3-05-moiety, for example, any one of a C3-moiety, or a C5-moiety.

In an embodiment, preferred compounds of formula I or II have $R^3$, $R^4$ and $R^5$, independently of each other, which are selected from H, halogen, C1-C6-alkoxy and C1-C6-alkyl.

In an embodiment, preferred compounds of formula I or II are where W, X and Y are each CH.

In an embodiment, preferred compounds formula I or II are where one of W, X or Y is selected from halo-C (e.g. F—C), C1-C3-alkyl-C (e.g. $CH_3C$), C1-C3-alkoxy-C (e.g. $CH_3OC$), C1-C3-haloalkyl (e.g. $CF_3C$) and remaining two are each CH; in a preferred embodiment Y is selected from halo-C (e.g. F—C) and W and X are each CH.

In an embodiment, $R^2$ in formula I or II is a halogen, preferably Cl or F. In a preferred embodiment $R^2$ in formula I or II is F. In a further preferred embodiment $R^2$ in formula I or II is Cl.

In an embodiment, $R^5$ in formula I or II is halogen. In a preferred embodiment, $R^5$ in formula I or II is Cl or F.

In an embodiment, $R^6$ in formula I is C1-C3-alkyl, CN, OH, C1-C3-alkoxy, C2-C3-alkenyloxy, C2-C3-alkynyloxy, C3-C5-cycloalkyl, C3-C5-cycloakyl-C1-C3-alkyl, C2-C3-alkenyl, C2-C3-haloalkenyl, C2-C3-alkynyl, C2-C3-haloalkynyl, amino-C1-C3-alkyl, nitro-C1-C3-alkyl, cyano-C1-C3-alkyl, C1 or C3-haloalkyl, C1-C3-halolkoxy-C1-C3-alkyl, C1-C3-alkoxy-C1-C3-alkyl, C1-C3-alkylthio-C1-C3-alkyl, C1-C3-alkylsulfinyl-C1-C3-alkyl, C1-C3-alkylsulfonyl-C1-C3-alkyl, C1-C3-alkylcarbonyloxy-C1-C3-alkyl, C1-C3-alkylamino-C1-C3-alkyl, di(C1-C3)-alkylamino-C1-C3-alkyl, optionally substituted (preferably 1, 2 or 3 halo substituted) arylcarbonyloxy-C1-C3-alkyl, optionally substituted (preferably 1, 2 or 3 halo substituted) benzyl, optionally substituted (preferably 1, 2 or 3 halo substituted) benzyloxy, or optionally substituted (preferably 1, 2 or 3 halo substituted) heterocyclyl-C1-C3-alkyl, wherein the heterocyclyl group is a saturated, partially unsaturated or aromatic 5 or 6 membered ring containing, as ring members, one or two heteroatoms selected, independently of one another, from N, O and S. In a preferred embodiment, $R^6$ in formula I, is heterocyclyl-C1-C3-alkyl, wherein the heterocyclyl group is a saturated, partially unsaturated or aromatic 5 or 6 membered ring containing, as ring members, one or two heteroatoms selected, independently of one another, from N, O and S, which may be unsubstituted or substituted with one or two halogen substituents. In a further preferred embodiment, $R^6$ in formula I, is C1-C3-alkyl.

In an embodiment, $R^6$ in formula II is C3-C6-alkyl, C3-C5-cycloalkyl, C3-C5-cycloakyl-C1-C3-alkyl, C2-C3-haloalkenyl, C2-C3-alkynyl, C2-C3-haloalkynyl, nitro-C1-C3-alkyl, cyano-C1-C3-alkyl, C3-C4-haloalkyl, C1-C3-alkoxy-C1-C3-alkyl, C1-C3-alkylthio-C1-C3-alkyl, C1-C3-alkylsulfinyl-C1-C3-alkyl, C1-C3-alkylsulfonyl-C1-C3-alkyl, C1-C3-alkylcarbonyloxy-C1-C3-alkyl, di(C1-C3)-alkylamino-C1-C3-alkyl, optionally substituted (preferably 1, 2 or 3 halo substituted) benzyl, or optionally substituted (preferably 1, 2 or 3 halo substituted) heterocyclyl-C1-C3-alkyl, wherein the heterocyclyl group is a saturated, partially unsaturated or aromatic 5 or 6 membered ring containing, as ring members, one or two heteroatoms selected, independently of one another, from N, O and S. In a preferred embodiment, $R^6$ in formula II, is heterocyclyl-C1-C3-alkyl, wherein the heterocyclyl group is a saturated, partially unsaturated or aromatic 5 or 6 membered ring containing, as ring members, one or two heteroatoms selected, independently of one another, from N, O and S, which may be unsubstituted or substituted with one or two halogen substituents. In a further preferred embodiment, $R^6$ in formula II, is C3-C6-alkyl.

In an embodiment, for compounds of formula I, $R^2$ is Cl or F, W, X and Y are each CH and $R^6$ is selected from cyclopropyl, allyl, propargyl, methyl, ethyl and propyl.

In an embodiment, for compounds of formula II, $R^2$ is Cl or F, W, X and Y are each CH and $R^6$ is either propyl and cycylopropyl-methyl.

Specific examples of formulae I and 2 are disclosed in the Tables below.

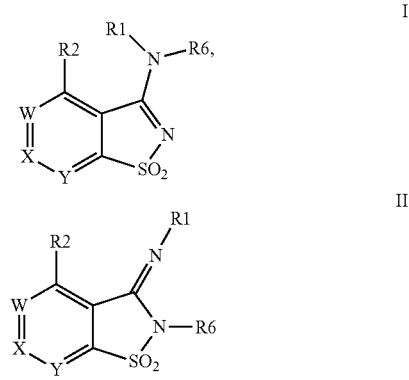

Table 1.1: A compound of formula (I), wherein W, X and Y are C—H, R1 is H, R2 is fluorine and the values for R6 are as given in the Table A. Table 1.2: A compound of formula (I), wherein W, X and Y are C—H, R1 is H, R2 is chlorine and the values for R6 are as given in the Table A.

Table 1.3: A compound of formula (I), wherein W, X and Y are C—H, R1 is H, R2 is bromine and the values for R6 are as given in the Table A.

Table 1.4: A compound of formula (I), wherein W, X and Y are C—H, R1 is H, R2 is iodine and the values for R6 are as given in the Table A.

Table 1.5: A compound of formula (I), wherein W is C—F, X and Y are C—H, R1 is H, R2 is fluorine and the values for R6 are as given in the Table A.

Table 1.6: A compound of formula (I), wherein W is C—F, X and Y are C—H, R1 is H, R2 is chlorine and the values for R6 are as given in the Table A.

Table 1.7: A compound of formula (I), wherein W is C—F, X and Y are C—H, R1 is H, R2 is bromine and the values for R6 are as given in the Table A.

Table 1.8: A compound of formula (I), wherein W is C—F, X and Y are C—H, R1 is H, R2 is iodine and the values for R6 are as given in the Table A.

Table 1.9: A compound of formula (I), wherein X is C—F, W and Y are C—H, R1 is H, R2 is fluorine and the values for R6 are as given in the Table A.

Table 1.10: A compound of formula (I), wherein X is C—F, W and Y are C—H, R1 is H, R2 is chlorine and the values for R6 are as given in the Table A.

Table 1.11: A compound of formula (I), wherein X is C—F, W and Y are C—H, R1 is H, R2 is bromine and the values for R6 are as given in the Table A.

Table 1.12: A compound of formula (I), wherein X is C—F, W and Y are C—H, R1 is H, R2 is iodine and the values for R6 are as given in the Table A.

Table 1.13: A compound of formula (I), wherein Y is C—F, W and X are C—H, R1 is H, R2 is fluorine and the values for R6 are as given in the Table A.

Table 1.14: A compound of formula (I), wherein Y is C—F, W and X are C—H, R1 is H, R2 is chlorine and the values for R6 are as given in the Table A.

Table 1.15: A compound of formula (I), wherein Y is C—F, W and X are C—H, R1 is H, R2 is bromine and the values for R6 are as given in the Table A.

Table 1.16: A compound of formula (I), wherein Y is C—F, W and X are C—H, R1 is H, R2 is iodine and the values for R6 are as given in the Table A.

Table 1.17: A compound of formula (I), wherein W is C—$CH_3$, X and Y are C—H, R1 is H, R2 is fluorine and the values for R6 are as given in the Table A.

Table 1.18: A compound of formula (I), wherein W is C—$CH_3$, X and Y are C—H, R1 is H, R2 is chlorine and the values for R6 are as given in the Table A.

Table 1.19: A compound of formula (I), wherein W is C—$CH_3$, X and Y are C—H, R1 is H, R2 is bromine and the values for R6 are as given in the Table A.

Table 1.20: A compound of formula (I), wherein W is C—$CH_3$, X and Y are C—H, R1 is H, R2 is iodine and the values for R6 are as given in the Table A.

Table 1.21: A compound of formula (I), wherein X is C—$CH_3$, W and Y are C—H, R1 is H, R2 is fluorine and the values for R6 are as given in the Table A.

Table 1.22: A compound of formula (I), wherein X is C—$CH_3$, W and Y are C—H, R1 is H, R2 is chlorine and the values for R6 are as given in the Table A.

Table 1.23: A compound of formula (I), wherein X is C—$CH_3$, W and Y are C—H, R1 is H, R2 is bromine and the values for R6 are as given in the Table A.

Table 1.24: A compound of formula (I), wherein X is C—$CH_3$, W and Y are C—H, R1 is H, R2 is iodine and the values for R6 are as given in the Table A.

Table 1.25: A compound of formula (I), wherein Y is C—$CH_3$, W and X are C—H, R1 is H, R2 is fluorine and the values for R6 are as given in the Table A.

Table 1.26: A compound of formula (I), wherein Y is C—$CH_3$, W and X are C—H, R1 is H, R2 is chlorine and the values for R6 are as given in the Table A.

Table 1.27: A compound of formula (I), wherein Y is C—$CH_3$, W and X are C—H, R1 is H, R2 is bromine and the values for R6 are as given in the Table A.

Table 1.28: A compound of formula (I), wherein Y is C—$CH_3$, W and X are C—H, R1 is H, R2 is iodine and the values for R6 are as given in the Table A.

Table 1.29: A compound of formula (I), wherein W is C—$OCH_3$, X and Y are C—H, R1 is H, R2 is fluorine and the values for R6 are as given in the Table A.

Table 1.30: A compound of formula (I), wherein W is C—$OCH_3$, X and Y are C—H, R1 is H, R2 is chlorine and the values for R6 are as given in the Table A.

Table 1.31: A compound of formula (I), wherein W is C—$OCH_3$, X and Y are C—H, R1 is H, R2 is bromine and the values for R6 are as given in the Table A.

Table 1.32: A compound of formula (I), wherein W is C—$OCH_3$, X and Y are C—H, R1 is H, R2 is iodine and the values for R6 are as given in the Table A.

Table 1.33: A compound of formula (I), wherein X is C—$OCH_3$, W and Y are C—H, R1 is H, R2 is fluorine and the values for R6 are as given in the Table A.

Table 1.34: A compound of formula (I), wherein X is C—$OCH_3$, W and Y are C—H, R1 is H, R2 is chlorine and the values for R6 are as given in the Table A.

Table 1.35: A compound of formula (I), wherein X is C—$OCH_3$, W and Y are C—H, R1 is H, R2 is bromine and the values for R6 are as given in the Table A.

Table 1.36: A compound of formula (I), wherein X is C—$OCH_3$, W and Y are C—H, R1 is H, R2 is iodine and the values for R6 are as given in the Table A.

Table 1.37: A compound of formula (I), wherein Y is C—$OCH_3$, W and X are C—H, R1 is H, R2 is fluorine and the values for R6 are as given in the Table A.

Table 1.38: A compound of formula (I), wherein Y is C—$OCH_3$, W and X are C—H, R1 is H, R2 is chlorine and the values for R6 are as given in the Table A.

Table 1.39: A compound of formula (I), wherein Y is C—$OCH_3$, W and X are C—H, R1 is H, R2 is bromine and the values for R6 are as given in the Table A.

Table 1.40: A compound of formula (I), wherein Y is C—$OCH_3$, W and X are C—H, R1 is H, R2 is iodine and the values for R6 are as given in the Table A.

Table 1.41: A compound of formula (I), wherein W is C—$CF_3$, X and Y are C—H, R1 is H, R2 is fluorine and the values for R6 are as given in the Table A.

Table 1.42: A compound of formula (I), wherein W is C—$CF_3$, X and Y are C—H, R1 is H, R2 is chlorine and the values for R6 are as given in the Table A.

Table 1.43: A compound of formula (I), wherein W is C—$CF_3$, X and Y are C—H, R1 is H, R2 is bromine and the values for R6 are as given in the Table A.

Table 1.44: A compound of formula (I), wherein W is C—$CF_3$, X and Y are C—H, R1 is H, R2 is iodine and the values for R6 are as given in the Table A.

Table 1.45: A compound of formula (I), wherein X is C—$CF_3$, W and Y are C—H, R1 is H, R2 is fluorine and the values for R6 are as given in the Table A.

Table 1.46: A compound of formula (I), wherein X is C—$CF_3$, W and Y are C—H, R1 is H, R2 is chlorine and the values for R6 are as given in the Table A.

Table 1.47: A compound of formula (I), wherein X is C—$CF_3$, W and Y are C—H, R1 is H, R2 is bromine and the values for R6 are as given in the Table A.

Table 1.48: A compound of formula (I), wherein X is C—$CF_3$, W and Y are C—H, R1 is H, R2 is iodine and the values for R6 are as given in the Table A.

Table 1.49: A compound of formula (I), wherein Y is C—$CF_3$, W and X are C—H, R1 is H, R2 is fluorine and the values for R6 are as given in the Table A.

Table 1.50: A compound of formula (I), wherein Y is C—$CF_3$, W and X are C—H, R1 is H, R2 is chlorine and the values for R6 are as given in the Table A.

Table 1.51: A compound of formula (I), wherein Y is C—$CF_3$, W and X are C—H, R1 is H, R2 is bromine and the values for R6 are as given in the Table A.

Table 1.52: A compound of formula (I), wherein Y is C—$CF_3$, W and X are C—H, R1 is H, R2 is iodine and the values for R6 are as given in the Table A.

Table 1.53: A compound of formula (II), wherein W, X and Y are C—H, R1 is H, R2 is fluorine and the values for R6 are as given in the Table B.

Table 1.54: A compound of formula (II), wherein W, X and Y are C—H, R1 is H, R2 is chlorine and the values for R6 are as given in the Table B.

Table 1.55: A compound of formula (II), wherein W, X and Y are C—H, R1 is H, R2 is bromine and the values for R6 are as given in the Table B.

Table 1.56: A compound of formula (II), wherein W, X and Y are C—H, R1 is H, R2 is iodine and the values for R6 are as given in the Table B.

Table 1.57: A compound of formula (II), wherein W is C—F, X and Y are C—H, R1 is H, R2 is fluorine and the values for R6 are as given in the Table B.

Table 1.58: A compound of formula (II), wherein W is C—F, X and Y are C—H, R1 is H, R2 is chlorine and the values for R6 are as given in the Table B.

Table 1.59: A compound of formula (II), wherein W is C—F, X and Y are C—H, R1 is H, R2 is bromine and the values for R6 are as given in the Table B.

Table 1.60: A compound of formula (II), wherein W is C—F, X and Y are C—H, R1 is H, R2 is iodine and the values for R6 are as given in the Table B.

Table 1.61: A compound of formula (II), wherein X is C—F, W and Y are C—H, R1 is H, R2 is fluorine and the values for R6 are as given in the Table B.

Table 1.62: A compound of formula (II), wherein X is C—F, W and Y are C—H, R1 is H, R2 is chlorine and the values for R6 are as given in the Table B.

Table 1.63: A compound of formula (II), wherein X is C—F, W and Y are C—H, R1 is H, R2 is bromine and the values for R6 are as given in the Table B.

Table 1.64: A compound of formula (II), wherein X is C—F, W and Y are C—H, R1 is H, R2 is iodine and the values for R6 are as given in the Table B.

Table 1.65: A compound of formula (II), wherein Y is C—F, W and X are C—H, R1 is H, R2 is fluorine and the values for R6 are as given in the Table B.

Table 1.66: A compound of formula (II), wherein Y is C—F, W and X are C—H, R1 is H, R2 is chlorine and the values for R6 are as given in the Table B.

Table 1.67: A compound of formula (II), wherein Y is C—F, W and X are C—H, R1 is H, R2 is bromine and the values for R6 are as given in the Table B.

Table 1.68: A compound of formula (II), wherein Y is C—F, W and X are C—H, R1 is H, R2 is iodine and the values for R6 are as given in the Table B.

Table 1.69: A compound of formula (II), wherein W is C—$CH_3$, X and Y are C—H, R1 is H, R2 is fluorine and the values for R6 are as given in the Table B.

Table 1.70: A compound of formula (II), wherein W is C—$CH_3$, X and Y are C—H, R1 is H, R2 is chlorine and the values for R6 are as given in the Table B.

Table 1.71: A compound of formula (II), wherein W is C—$CH_3$, X and Y are C—H, R1 is H, R2 is bromine and the values for R6 are as given in the Table B.

Table 1.72: A compound of formula (II), wherein W is C—$CH_3$, X and Y are C—H, R1 is H, R2 is iodine and the values for R6 are as given in the Table B.

Table 1.73: A compound of formula (I), wherein X is C—$CH_3$, W and Y are C—H, R1 is H, R2 is fluorine and the values for R6 are as given in the Table B.

Table 1.74: A compound of formula (II), wherein X is C—$CH_3$, W and Y are C—H, R1 is H, R2 is chlorine and the values for R6 are as given in the Table B.

Table 1.75: A compound of formula (II), wherein X is C—$CH_3$, W and Y are C—H, R1 is H, R2 is bromine and the values for R6 are as given in the Table B.

Table 1.76: A compound of formula (II), wherein X is C—$CH_3$, W and Y are C—H, R1 is H, R2 is iodine and the values for R6 are as given in the Table B.

Table 1.77: A compound of formula (II), wherein Y is C—$CH_3$, W and X are C—H, R1 is H, R2 is fluorine and the values for R6 are as given in the Table B.

Table 1.78: A compound of formula (II), wherein Y is C—$CH_3$, W and X are C—H, R1 is H, R2 is chlorine and the values for R6 are as given in the Table B.

Table 1.79: A compound of formula (II), wherein Y is C—$CH_3$, W and X are C—H, R1 is H, R2 is bromine and the values for R6 are as given in the Table B.

Table 1.80: A compound of formula (II), wherein Y is C—$CH_3$, W and X are C—H, R1 is H, R2 is iodine and the values for R6 are as given in the Table B.

Table 1.81: A compound of formula (II), wherein W is C—$OCH_3$, X and Y are C—H, R1 is H, R2 is fluorine and the values for R6 are as given in the Table B.

Table 1.82: A compound of formula (II), wherein W is C—$OCH_3$, X and Y are C—H, R1 is H, R2 is chlorine and the values for R6 are as given in the Table B.

Table 1.83: A compound of formula (II), wherein W is C—$OCH_3$, X and Y are C—H, R1 is H, R2 is bromine and the values for R6 are as given in the Table B.

Table 1.84: A compound of formula (II), wherein W is C—$OCH_3$, X and Y are C—H, R1 is H, R2 is iodine and the values for R6 are as given in the Table B.

Table 1.85: A compound of formula (II), wherein X is C—$OCH_3$, W and Y are C—H, R1 is H, R2 is fluorine and the values for R6 are as given in the Table B.

Table 1.86: A compound of formula (II), wherein X is C—$OCH_3$, W and Y are C—H, R1 is H, R2 is chlorine and the values for R6 are as given in the Table B.

Table 1.87: A compound of formula (II), wherein X is C—$OCH_3$, W and Y are C—H, R1 is H, R2 is bromine and the values for R6 are as given in the Table B.

Table 1.88: A compound of formula (II), wherein X is C—$OCH_3$, W and Y are C—H, R1 is H, R2 is iodine and the values for R6 are as given in the Table B.

Table 1.89: A compound of formula (II), wherein Y is C—$OCH_3$, W and X are C—H, R1 is H, R2 is fluorine and the values for R6 are as given in the Table B.

Table 1.90: A compound of formula (Ii), wherein Y is C—$OCH_3$, W and X are C—H, R1 is H, R2 is chlorine and the values for R6 are as given in the Table B.

Table 1.91: A compound of formula (II), wherein Y is C—$OCH_3$, W and X are C—H, R1 is H, R2 is bromine and the values for R6 are as given in the Table B.

Table 1.92: A compound of formula (II), wherein Y is C—$OCH_3$, W and X are C—H, R1 is H, R2 is iodine and the values for R6 are as given in the Table B.

Table 1.93: A compound of formula (II), wherein W is C—$CF_3$, X and Y are C—H, R1 is H, R2 is fluorine and the values for R6 are as given in the Table B.

Table 1.94: A compound of formula (II), wherein W is C—$CF_3$, X and Y are C—H, R1 is H, R2 is chlorine and the values for R6 are as given in the Table B.

Table 1.95: A compound of formula (II), wherein W is C—$CF_3$, X and Y are C—H, R1 is H, R2 is bromine and the values for R6 are as given in the Table B.

Table 1.96: A compound of formula (II), wherein W is C—$CF_3$, X and Y are C—H, R1 is H, R2 is iodine and the values for R6 are as given in the Table B.

Table 1.97: A compound of formula (I), wherein X is C—$CF_3$, W and Y are C—H, R1 is H, R2 is fluorine and the values for R6 are as given in the Table B.

Table 1.98: A compound of formula (II), wherein X is C—CF₃, W and Y are C—H, R1 is H, R2 is chlorine and the values for R6 are as given in the Table B.

Table 1.99: A compound of formula (II), wherein X is C—CF₃, W and Y are C—H, R1 is H, R2 is bromine and the values for R6 are as given in the Table B.

Table 1.100: A compound of formula (II), wherein X is C—CF₃, W and Y are C—H, R1 is H, R2 is iodine and the values for R6 are as given in the Table B.

Table 1.101: A compound of formula (II), wherein Y is C—CF₃, W and X are C—H, R1 is H, R2 is fluorine and the values for R6 are as given in the Table B.

Table 1.102: A compound of formula (II), wherein Y is C—CF₃, W and X are C—H, R1 is H, R2 is chlorine and the values for R6 are as given in the Table B.

Table 1.103: A compound of formula (II), wherein Y is C—CF₃, W and X are C—H, R1 is H, R2 is bromine and the values for R6 are as given in the Table B.

Table 1.104: A compound of formula (II), wherein Y is C—CF₃, W and X are C—H, R1 is H, R2 is iodine and the values for R6 are as given in the Table B.

TABLE A

R6

—CN
—CH₃
—CH₂CH₃
—CH₂CH₂CH₃
—CH(CH₃)₂

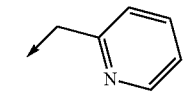

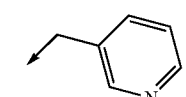

—CH=CH₂
—CH₂CH=CH₂
—CH₂C≡CH
—CH₂CH=CF₂
—CH₂C≡C—I
—CH₂CN
—CH₂NO₂
—CH₂NH₂
—CH₂CH₂CCl₃
—CH₂CH₂OCH₃
—CH₂CH₂OCH₂CH₂Cl
—CH₂CH₂SCH₃
—CH₂CH₂S(O)CH₃
—CH₂CH₂S(O)₂CH₃
—CH₂CO₂CH₃
—CH₂CH₂NH(CH₃)
—CH₂CH₂N(CH₃)₂
—CH₂CH₂OC(O)CH₃

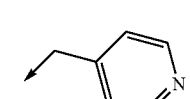

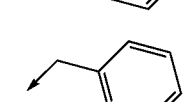

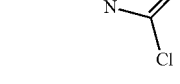

TABLE A-continued

R6

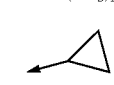

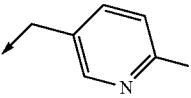

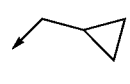

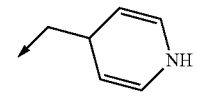

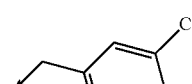

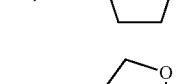

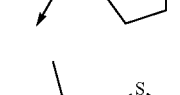

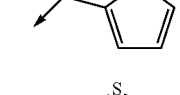

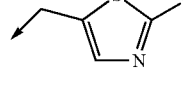

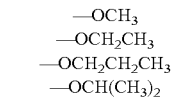

—OH
—OCH₃
—OCH₂CH₃
—OCH₂CH₂CH₃
—OCH(CH₃)₂
—OCH₂CH=CH₂
—OCH₂C≡CH

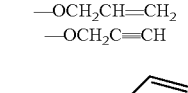

TABLE B

| R6 |
|---|
| —CN |
| —CH$_2$CH$_2$CH$_3$ |
| —CH(CH$_3$)$_2$ |
| cyclopropyl |
| cyclopropylmethyl |
| —CH$_2$C≡CH |
| —CH$_2$CH$_2$CN |
| —CH$_2$CH=CF$_2$ |
| —CH$_2$C≡C—I |
| —CH$_2$CH$_2$NO$_2$ |
| —CH$_2$CH$_2$CCl$_3$ |
| —CH$_2$CH$_2$OCH$_3$ |
| —CH$_2$CH$_2$SCH$_3$ |
| —CH$_2$CH$_2$S(O)CH$_3$ |
| —CH$_2$CH$_2$S(O)$_2$CH$_3$ |
| —CH$_2$CH$_2$CO$_2$CH$_3$ |
| —CH$_2$CH$_2$N(CH$_3$)$_2$ |
| benzyl |
| 4-chlorobenzyl |
| 2-pyridylmethyl |
| 3-pyridylmethyl |
| 4-pyridylmethyl |
| 4-(1,4-dihydropyridyl)methyl |
| (6-chloro-2-pyridyl)methyl |
| (6-chloro-3-pyridyl)methyl |
| (2-chloro-4-pyridyl)methyl |

TABLE B-continued

| R6 |
|---|
| (tetrahydrofuran-2-yl)methyl |
| (tetrahydrofuran-3-yl)methyl |
| 1-(thiophen-2-yl)ethyl |
| (2-chlorothiazol-5-yl)methyl |

The following example is given by way of illustration and not by way of limitation of the invention.

Compounds of formula I or II, in which W, X, Y, R$^2$, R1 and R$^6$ are defined as in the first aspect can be prepared by reacting 3-Chloro-benzo[d]-isothiazole 1,1-dioxides A with a primary amine B. Hal is halogen, preferably chlorine or bromine, most preferred chlorine.

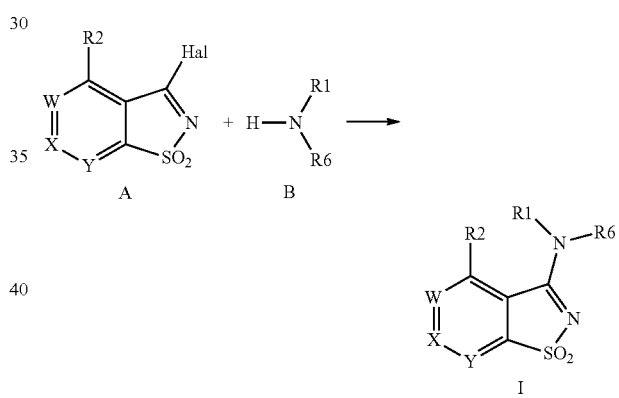

These reactions can be carried out similarly to standard methods described in the past, for example in the publication by Duphar EP 33984, by BASF WO 07113119 or in the literature by C. W. Whitehead, Journal of Organic Chemistry, 25, 413-16; 1960 or by H. B. Rode, Pharmazie, 60(10), 723-731; 2005.

3-Chloro-benzo[d]-isothiazole 1,1-dioxides A can be prepared by reacting sacharines C with a chlorinating agent such as SOCl$_2$, PCl$_5$/POCl$_3$ as described by H. B. Rode, Pharmazie, 60(10), 723-731; 2005.

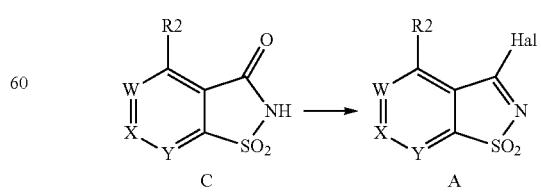

Substituted saccharines C can be prepared by reacting 2-chlorosulfonyl-benzoic acid esters D with ammonia as described by Desai, Ranjit C, Journal of Organic Chemistry (1994), 59(23), 7161-3 or by Naoyuki Masuda, Bioorgaic & Medicinal Chemistry 13 (2005) 949-961

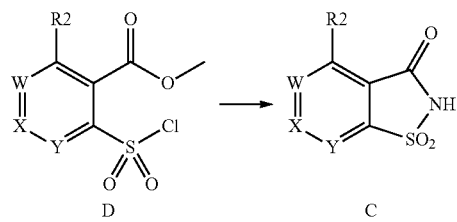

The latter article also describes the synthesis of 2-chlorosulfonyl-benzoic acid esters D from the corresponding methyl anthranilates E via diazotation and subsequent chlorosulfonylation. A similar procedure is described by M. L. Trudell et al. in Journal of Heterocyclic Chemistry, 2004, 41, 435-438.

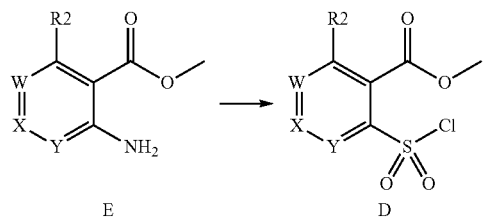

In cases where the methyl anthranilates E are not commercially available, they can be prepared from the corresponding 2-nitro benzoic acid methyl ester F by catalytic hydrogenation as described by J. F. W. Keana et al. in Bioorganic & Medicinal Chemistry 11 (2003) 1769-1780 or by reducing agents like $SnCl_2$ or $Na_2(S_2O_4)$ as described by F. H. Jung, J. Med. Chem. 2006, 49, 955-970 or by M. H. Rabinowitz et al., J. Med. Chem. 2006, 49, 6371-6390

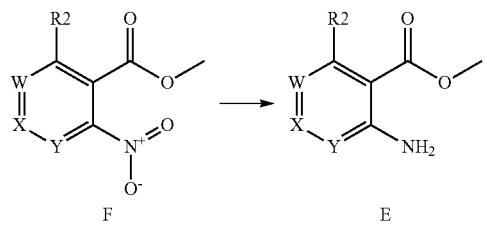

Alternatively, sacharines (C) can be prepared by cleavage of the corresponding N-t-butyl saccarines G via heating with a strong acid such as trifluoracetic acid similiar to the method described by K. F. Burri, Helvetica Chimia acta, 1990, 73, 69-80.

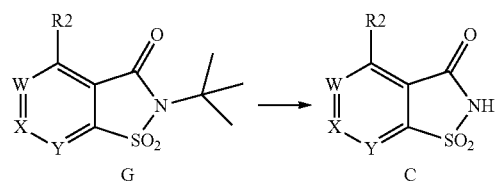

N-t-butyl saccharines G can be prepared from compounds of formula J in which R6 is t-butyl by directed ortho metallation with bases such as butyllithium or lithiumdiisopropylamide and subsequent trapping of the metallated species with carbon dioxide under ring closure. The procedure is described by D. Becker et al., Tetrahedron, 1992, 2515-2522. The metallation can be carried out as descibed by N. Murugesan et al., Journal of Medicinal Chemisry, 1998, 41, 5198-5212.

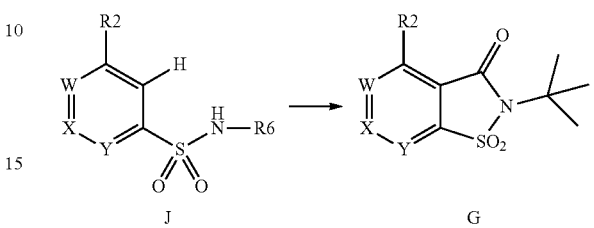

Alternatively compounds of formula I or II, in which W, X, Y, R2, R1 and R6 are defined as in the first aspect can be prepared from compounds of formula (Ia) using standard methods like alkylation or reductive amination. Similar conversions were already described in the past, for example in the publication by Duphar EP 33984.

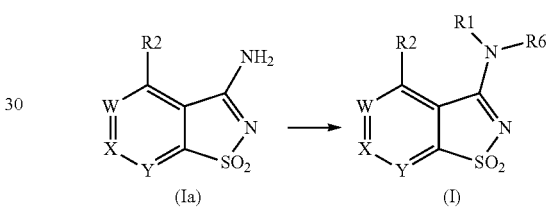

Compounds of formula (Ia) or formula (IIa) can be prepared from sulfonyl chlorides L via sulfonamides H or K by cyclisation under basic conditions.

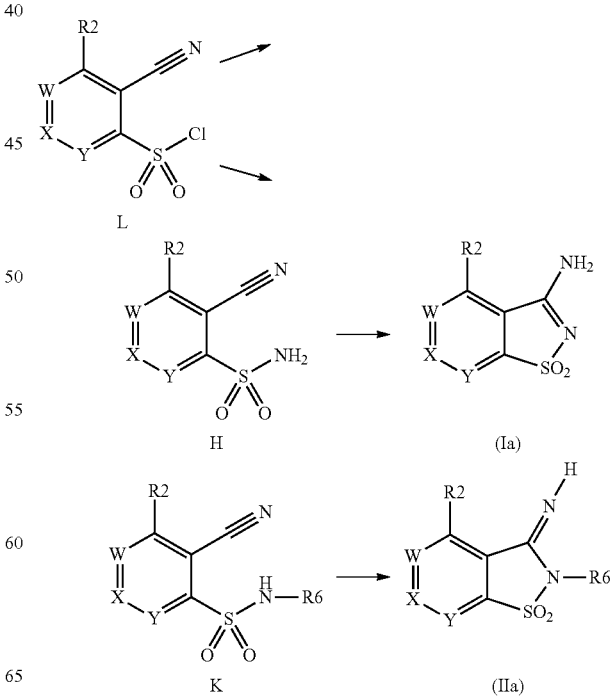

Alternatively compounds of formula (I), in which W, X, Y, R2, and R6 are defined as in the first aspect and R1 is hydrogen can be prepared from compounds of formula M via a reaction with primary amine at elevated temperature. The reaction can be carried out either neat or in a suitable solvent, preferably a polar, high boiling solvent such as THF or dioxane. Preferably the reaction is carried out neat. In cases were the reaction is carried out neat, the preferred temperature is between room temperature and the boiling point of the amine. in cases were the reaction is carried out in a solvent, the preferred temperature is between room temperature and the boling point of the solvent. The substituents R99 in this method are preferentially an alkyl substituent such as methyl or ethyl.

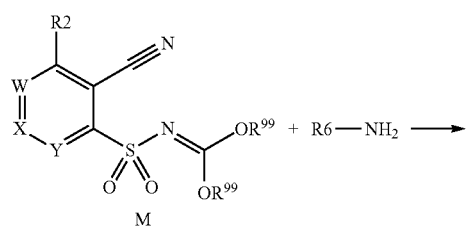

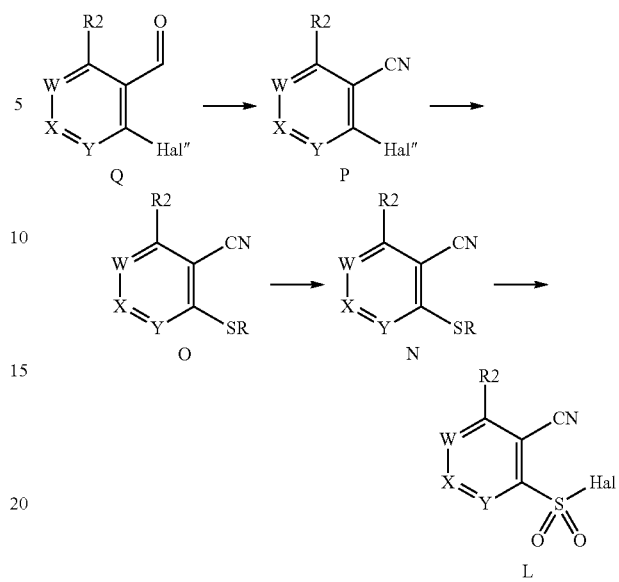

Alternatively sulfonylhalides of formula L can be prepared from amino compounds of formula R.

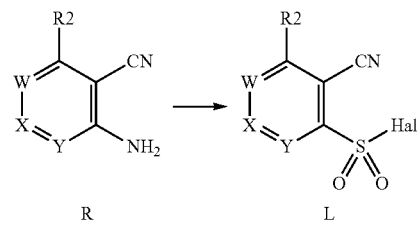

The amino group in compound R is converted into the corresponding diazonium salt followed by reacting the diazonium salt with dioxide in the presence of cupric(II)chloride to afford the sulfonylchloride L.

Suitable nitrosating agents are nitrosium tetrafluoroborate, nitrosyl chloride, nitrosyl sulfuric acid, alkyl nitrites, such as tert.-butyl nitrite, or salts of nitrous acid, such as sodium nitrite. Preferably sodium nitrite is used.

In general, sulfur dioxide is dissolved in glacial acetic acid. The diazonium salt can also react with a mixture of cupric (I) cyanate and sodium cyanate to afford the cyanate compound, which is treated with sodium sulfide to afford the disulfide compound. The disulfide compound is converted with nitrous acid in the presence of chlorine into the sulfonylchloride L.

In cases where the amino compounds of formula R are not commercially available, they can be prepared from the corresponding 2-nitro compounds S by similar methodes as described for the preparation of amino compounds E.

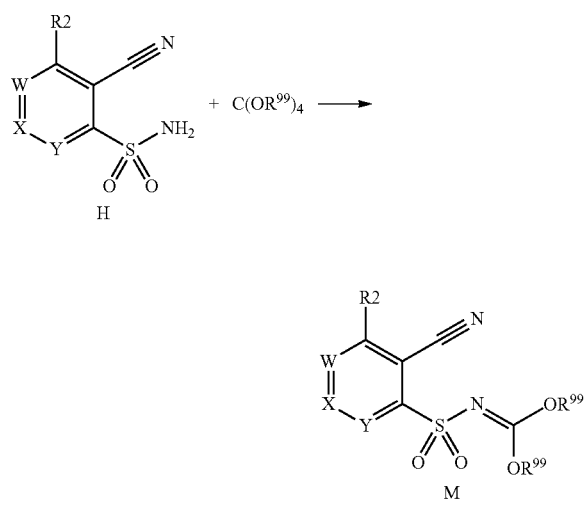

Imidate compounds of formula M can be obtained by reacting a sulfonamide of formula H with a carbonic acid orthoester in a process similarly described by R. F. Meyer, Journal of Organic Chemistry, 1963, 28, 2902-2903.

New 2-cyano-sulfonylhalides L can be prepared by the methods described hereafter.

Similar to standard procedures, for example as described in the publication WO07/014913 by BASF, compounds L, N, O and P can be prepared starting from compound Q (when W, X, Y and R2 are as defined in the first aspect).

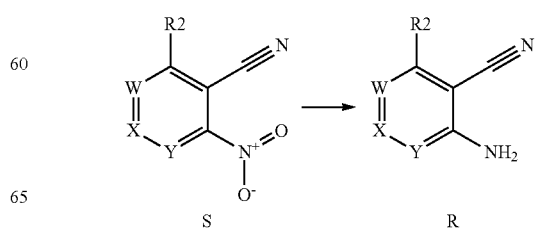

Alternatively amino compounds of formula R can be prepared from compounds of formula T via oximes of formula U as described by James B. Campbell, Synthetic Communications (1989), 19(13-14), 2255-63.

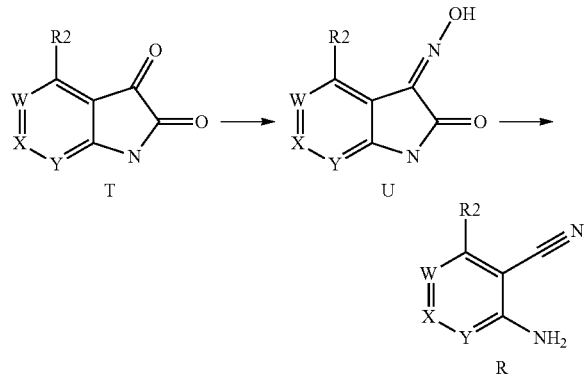

Certain compounds of formula (I) or (II) can be prepared from compounds of formula (I) or (II) where any one of W, X, and Y is C-halogen and halogen is chlorine, bromine or iodine by metal catalysed cross coupling reactions as for example cyanation, Sonogashira, Stille, Heck or Suzuki cross coupling reactions. These reactions can be carried out similarly to standard procedures described in the literature. Many examples can be found in the reference book "Metal Catalyzed Cross Coupling Reactions" 2nd ed.; Diederich, F., de Meijere, A., Eds.; Wiley-VCH: Weinheim, Germany, 2004

As an example the introduction of the group R5 is shown in scheme

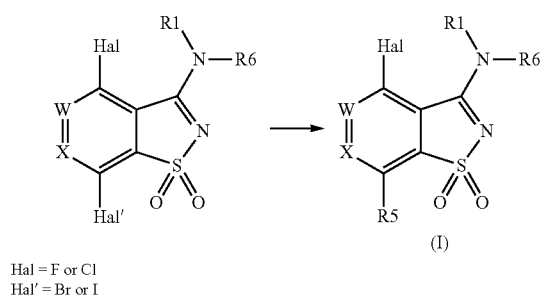

Hal = F or Cl
Hal' = Br or I

A skilled person would understand that appropriate changes to reaction conditions described above may be required for a specific cyano-substituted phenyl compounds and the corresponding nitrogenous derivative compounds thereof of formula I or II or II.

A compound of formula I or II or II can be converted in a manner known per se into another compound of formula I or II or II respectively by replacing one or more substituents of the starting compound of formula I or II or II respectively in the customary manner by (an)other substituent(s) defined herein.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I or II or II can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I or II can be converted in the customary manner into the free compounds of formula I or II or II respectively, acid addition salts, for example, by treatment with a suitable basic compound or with a suitable ion exchanger reagent and salts with bases, for example, by treatment with a suitable acid or with a suitable ion exchanger reagent.

Salts of compounds of formula I or II can be converted in a manner known per se into other salts of compounds of formula I or II respectively, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I or II, which have salt-forming properties can be obtained in free form or in the form of salts.

Salts of the compounds of the formula I or II which are suitable for the use according to the invention are especially agriculturally acceptable salts. They can be formed in a customary method, e. g. by reacting the compound with an acid of the anion in question.

Suitable agriculturally useful salts are especially the salts of those cations or the acid addition salts of those acids whose cations and anions, respectively, do not have any adverse effect on the action of the compounds according to the present invention, which are useful for combating harmful insects, arachnids and/or nematodes. Thus, suitable cations are in particular the ions of the alkali metals, preferably lithium, sodium and potassium, of the alkaline earth metals, preferably calcium, magnesium and barium, and of the transition metals, preferably manganese, copper, zinc and iron, and also the ammonium ion which may, if desired, carry one to four C1-C4-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri(C1-C4-alkyl) sulfonium, and sulfoxonium ions, preferably tri (Ci-C4-alkyl) sulfoxonium.

Anions of useful acid addition salts are primarily chloride, bromide, fluoride, hydrogen sulfate, sulfate, dihydrogen phosphate, hydride, hydroxide, hydrogen phosphate, phosphate, nitrate, hydrogen carbonate, carbonate, hexafluorosilicate, hexafluorophosphate, benzoate, and the anions of C1-C4-alkanoic acids, preferably formate, acetate, propionate and butyrate. They can be formed by reacting the compounds of the formula I or II with an acid of the corresponding anion, preferably of hydrochloric acid, hydrobromic acid, sulfuric acid, phosphoric acid or nitric acid. Also suitable salts include adducts of the formula I or II, such as maleic acid, dimaleic acid, fumaric acid, difumaric acid, and methane sulfonic acid.

The compounds of formula I or II and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I or II, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I or II and, where appropriate, the tautomers thereof, in each case in free form or in salt form, can, if appropriate, also be obtained in the form of hydrates and/or include other solvents, for example those which may have been used for the crystallization of compounds which are present in solid form.

Also made available herein are novel intermediate compounds to the compounds of formula I or II.

The compounds I and II according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

In another aspect, the present invention relates to a method for controlling a pest in crop protection or for protecting a seed, a plant, parts of a plant and/or plant organs that grow at a later point in time against pest damage which comprises applying a compound of formula I or II as above defined or a composition thereof to the pest, to the plant, to the seed, to the part of a plant and/or plant organ and/or the environment of each thereof.

In another aspect, the present invention also relates to a method for controlling a pest which comprises applying a compound of formula I or II as above defined to the pest, material for protection and/or environment thereof. In a preferred embodiment, the present invention relates to a method wherein the material is selected from a raw material, such as wood, textile, floor covering and building material. In another preferred embodiment, the present invention relates to method wherein the pest is controlled against damaging stored goods. In further preferred embodiment, the present invention relates to a method wherein the pest is controlled in the hygiene sector, especially the protection of humans, domestic animals and productive livestock.

The compounds of the formula I or II and compositions thereof are suitable for efficiently controlling pests from the class Insecta, class Arachnida and/or class Nematoda, particularly in crop protection. In particular, they are suitable for controlling the following animal pests:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;*

Beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica balteata, Diabrotica longicornis, Diabrotica 12-punctata, Diabrotica virgifera, Epilachna varivestis, Epitrix hirtipennis, Eutinobothrus brasiliensis,*

*Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria;*

Dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;*

Thrips (Thysanoptera), e.g. *Frankliniella fusca, Frankliniella occidentalis, Frankliniella tritici, Scirtothrips citri, Thrips oryzae, Thrips palmi* and *Thrips tabaci;*

Hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;*

Heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;*

Homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae,*

*Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii;*

Termites (Isoptera), e.g. *Calotermes flavicollis, Leucotermes flavipes, Reticulitermes lucifugus* and *Termes natalensis;*

Orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp., such as *Aculus schlechtendali, Phyllocoptrata oleivora* and *Eriophyes sheldoni; Tarsonemidae* spp., such as *Phytonemus pallidus* and *Polyphagotarsonemus latus; Tenuipalpidae* spp., such as *Brevipalpus phoenicis; Tetranychidae* spp., such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;* and Nematodes, including plant parasitic nematodes and nematodes living in the soil. Plant parasitic nematodes include, such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of formula I or II, and compositions containing them, can also be useful for molluscicidal action, especially against slugs. Molluscs which may be controlled by methods and compositions of the present invention are preferably molluscs comprised in the gastropod class, more preferably the subclass pulmonata, even more preferably snails and slugs, and most preferably include, for example, Ampullariidae; *Anion (A. ater, A. circumscriptus, A. hortensis, A. rufus)*; Bradybaenidae (*Bradybaena fruticum*); *Cepaea (C. hortensis, C. Nemoralis)*; ochlodina; *Deroceras (D. agrestis, D. empiricorum, D. laeve, D. reticulatum)*; *Discus*

(*D. rotundatus*); *Euomphalia*; *Galba* (*G. trunculata*); *Helicelia* (*H. itala, H. obvia*); Helicidae *Helicigona arbustorum*); *Helicodiscus*; *Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*. The combinations according to the present invention are particularly effective against *Deroceras*, such as *Deroceras reticulatum*.

The compounds of formula I or II, and compositions containing them, are especially suitable for the control of insects and/or nematodes. Moreover, the compounds of formula I or II (especially those disclosed in Table 1.1-1.104), and compositions containing them, are particularly suitable for the control of pests selected from the orders Homoptera, Lepidoptera, Diptera, Thysanoptera, and/or Nematoda.

In a preferred embodiment of the invention the compounds of formula I or II (such as those disclosed in Table 1.1-1.104), and compositions thereof can be used for controlling insects or arachnids, in particular insects of the orders Lepidoptera, Thysanoptera, Coleoptera and/or Homoptera and arachnids of the order Acarina, such as *Heliothis* spp., *Thrips* spp., *Diabrotica* spp., *Myzus* spp., *Aphis* spp. *Spodoptera* spp., *Plutella* spp., and *Tetranychidae* spp.

In another aspect, the present invention relates to a composition comprising the compound of formula I or II as above-defined and one or more customary formulation auxiliary.

For use in a method according to the present invention, the compounds of formula I or II can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I or II according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the compound of formula I or II with customary formulation auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
  solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-metyhl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.

carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen and benzyl alcohol hemiformal.

Suitable thickeners are compounds, which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol®23 (Rhone Poulenc) or Veegum® (from RT. Vanderbilt), or organic phyllosilicates, such as Attaclay® (from Engelhardt).

Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms.

Suitable biocides are, for example, based on isothiazolones such as the compounds marketed under the trademarks Proxel® from Avecia (or Arch) or Acticide® RS from Thor Chemie and Kathon® MK from Rohm and Haas.

Suitable antifreeze agents are organic polyols, for example ethylene glycol, propylene glycol or glycerol. These are usually employed in amounts of not more than 10% by weight, based on the total weight of the active compound composition.

If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I or II can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1% per weight. The active ingredients may also be used successfully in the ultra-low-volume process (ULV), it being possible to apply formulations comprising over 95% by weight of active ingredient, or even to apply the active ingredient without additives.

The following are examples of formulations:

1. Products for dilution with water. For seed treatment purposes, such products may be applied to the seed diluted or undiluted.

A) Water-soluble concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-dispersible granules and water-soluble granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-dispersible powders and water-soluble powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV solutions (UL)

10 parts by weight of the active compound is dissolved in 90 parts by weight of an organic solvent, for example xylene. This gives a product having 10% (w/w) of active compound, which is applied undiluted for foliar use.

Accordingly, a composition in the form of a formulation comprising a compound of formula I or II as defined in the first aspect and one or more customary formulation inerts is also provided herein; especially preferred is a seed treatment composition.

Various types of oils, wetters, adjuvants, herbicides, fungicides, other pesticides, or bactericides may be added to the compounds of the invention, if appropriate just immediately prior to use (tank mix). These agents usually are admixed with the agents according to the invention in a weight ratio of 1:10 to 10:1.

The compounds of formula I or II and compositions thereof may be applied with other active ingredients, for example with other pesticides, insecticides, fungicides, herbicides, fertilizers such as ammonium nitrate, urea, potash, and superphosphate, phytotoxicants and plant growth regulators, safeners and nematicides. These additional ingredients may be used sequentially or in combination with the above-described active ingredients, if appropriate added only immediately prior to use (tank mix) or provided as a formulated product (pre-mix). For example, the plant(s) may be sprayed with a composition comprising a compound of formula I or II either before or after being treated with other active ingredients. Generally a combination of active ingredients, including a compound of formula I or II, are used in seed treatment applications either as tank-mix or pre-mix compositions.

Each additional active ingredient can be admixed with a compound of formula I or II in a weight ratio of 1:10 to 10:1. In the case of two or more additional active ingredient and a compound of formula I or II, any two active ingredients (including a compound of formula I or II) can be in a weight ratio of 1:10 to 10:1. The resulting compositions frequently result in a broader pesticidal spectrum of action.

The following lists (M & F) of pesticides together with which the compounds of formula I or II according to the invention can be used and with which potential synergistic effects might be produced, is intended to illustrate the possible combinations, but not to impose any limitation:

M.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

M.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

M.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, empenthrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

M.4. Growth regulators: a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

M.5. Nicotinic receptor agonists/antagonists compounds: clothianidin, dinotefuran, imidacloprid, thiamethoxam, nitenpyram, acetamiprid, thiacloprid and AKD-1022;

M.6. GABA antagonist compounds: acetoprole, endosulfan, ethiprole, fipronil, vaniliprole, pyrafluprole, pyriprole, the phenylpyrazole compound of formula I or II$^2$

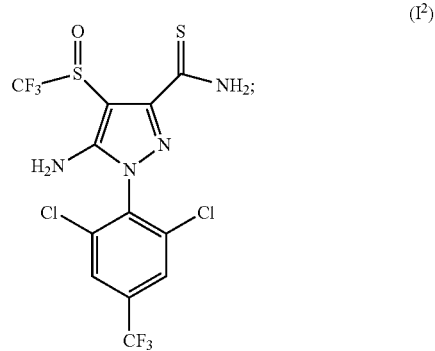 [SMILES: NC(=S)c1nn(-c2c(Cl)cc(C(F)(F)F)cc2Cl)c(N)c1S(=O)C(F)(F)F]

(I$^2$)

M.7. Macrocyclic lactone insecticides: abamectin, emamectin, milbemectin, lepimectin, spinosad;

M.8. METI I compounds: fenazaquin, pyridaben, tebufenpyrad, tolfenpyrad, flufenerim;

M.9. METI II and III compounds: acequinocyl, fluacyprim, hydramethylnon;

M.10. Uncoupler compounds: chlorfenapyr;

M.11. Oxidative phosphorylation inhibitor compounds: cyhexatin, diafenthiuron, fenbutatin oxide, propargite;

M.12. Moulting disruptor compounds: cyromazine;

M.13. Mixed Function Oxidase inhibitor compounds: piperonyl butoxide;

M.14. Sodium channel blocker compounds: indoxacarb, metaflumizone;

M.15. Various: amitraz, benclothiaz, bifenazate, cartap, flonicamid, pyridalyl, pymetrozine, sulfur, thiocyclam, flubendiamide, cyenopyrafen, flupyrazofos, cyflumetofen, amidoflumet, pyrifluquinazon, the aminoquinazolinone compound of formula I or II[3]

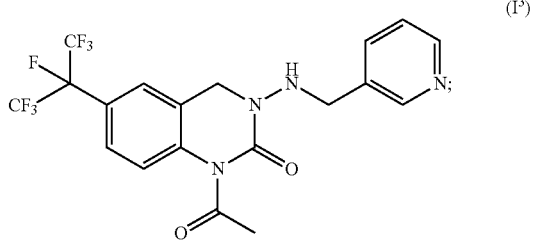

0 N-R'-2,2-dihalo-1-R"cyclo-propanecarboxamide-2-(2,6-dichloro-alpha,alpha,alpha -tri-fluoro-p-tolyl)hydrazone or N-R'-2,2-di(R''')propionamide-2-(2,6-dichloro-alpha,alpha,alpha-trifluoro-p-tolyl)-hydrazone, wherein R' is methyl or ethyl, halo is chloro or bromo, R" is hydrogen or methyl and R' is methyl or ethyl ; anthranilamide compounds as chlorantraniliprole or the compound of formula I or II[4]

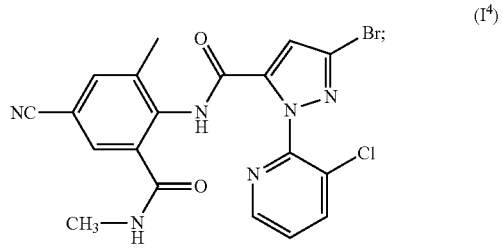 [SMILES: CNC(=O)c1cc(C#N)cc(C)c1NC(=O)c1cc(Br)nn1-c1ncccc1Cl]

malononitrile compounds as described in JP 2002 284608, WO 02/89579, WO 02/90320, WO 02/90321, WO 04/06677, WO 04/20399, JP 2004 99597, WO 05/68423, WO 05/68432, or WO 05/63694, especially the malononitrile compounds $CF_3(CH2)2C(CN)2CH2(CF2)3CF_2H$, $CF_3(CH2)2C(CN)2CH2(CF2)5CF_2H$, $CF_3(CH2)2C(CN)2(CH2)2C(CF_3)2F$, $CF_3(CH2)2C(CN)2(CH2)2(CF_2)3CF3$, $CF2H(CF2)3CH2C(CN)2CH2(CF2)3CF_2H$, $CF_3(CH2)2C(CN)2CH2(CF2)_3CF3$, $CF_3(CF_2)2CH2C(CN)2CH2(CF2)_3CF_2H$, and $CF_3CF_2CH2C(CN)2CH2(CF2)_3CF_2H$; and compound of formula I or II[5]

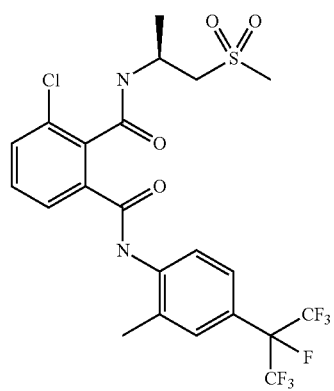

as described in WO07/101601.

The commercially available compounds of the group M may be found in The Pesticide Manual, 13th Edition, British Crop Protection Council (2003) among other publications.

Thioamides of formula I or II[2] and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p.237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180. The aminoquinazolinone compound of formula I or II[3] has been described in EPA 109 7932. Anthranilamides as the one of formula I or II[4] or as chloranthraniliprole and their preparations have been described in WO 01/70671; WO 02/48137; WO 03/24222, WO 03/15518, WO 04/67528; WO 04/33468; and WO 05/1 18552. The malononitrile compounds CF3(CH2)2C(CN)2CH2(CF2)3CF2H, F3(CH2)2C(CN)2CH2(CF2)5CF$_2$H, $CF_3$(CH2)2C(CN)2(CH2)2C(CF$_3$)2F, F$_3$(CH2)2C(CN)2(CH2)2(CF$_2$)3CF3, CF2H(CF2)3CH2C(CN)2CH2(CF2)3CF$_2$H, F$_3$(CH2)2C(CN)2CH2(CF2)$_3$CF3, CF$_3$(CF2)2CH2C(CN)2CH2(CF2)3CF$_2$H, and F$_3$CF2CH2C(CN)2CH2(CF2)3CF$_2$H have been described in WO 05/63694.

Fungicidal mixing partners are those selected from the group F consisting of

F.1 acylalanines such as benalaxyl, metalaxyl, ofurace, oxadixyl;

F.2 amine derivatives such as aldimorph, dodine, dodemorph, fenpropimorph, fenpropidin, guazatine, iminoctadine, spiroxamin, tridemorph;

F.3 anilinopyrimidines such as pyrimethanil, mepanipyrim or cyrodinyl; F.4 antibiotics such as cycloheximid, griseofulvin, kasugamycin, natamycin, polyoxin or streptomycin;

F.5 azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol;

F.6 dicarboximides such as iprodion, myclozolin, procymidon, vinclozolin;

F.7 dithiocarbamates such as ferbam, nabam, maneb, mancozeb, metam, metiram, propineb, polycarbamate, thiram, ziram, zineb;

F.8 heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine;

F.9 copper fungicides such as Bordeaux mixture, copper acetate, copper oxychloride, basic copper sulfate;

F.10 nitrophenyl derivatives such as binapacryl, dinocap, dinobuton, nitrophthalisopropyl;

F.11 phenylpyrroles such as fenpiclonil or fludioxonil;

F.12 strobilurins such as azoxystrobin, dimoxystrobin, fluoxastrobin, kresoxim-methyl, metominostrobin, orysastrobin, picoxystrobin or trifloxystrobin;

F.13 sulfenic acid derivatives such as captafol, captan, dichlofluanid, folpet, tolylfluanid;

F.14 cinnemamides and analogs such as dimethomorph, flumetover or flumorph;

F.15 sulfur, and other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentinacetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid.

Accordingly, a composition comprising a compound of formula I or II as defined in the first aspect and one or more active ingredients, such as other pesticides (as decribed above in list M and/or F), insecticides, fungicides, herbicides, fertilizers such as ammonium nitrate, urea, potash, and superphosphate, phytotoxicants and plant growth regulators, safeners and nematicides, and optionally one or more customary formulation inerts is also provided herein; especially preferred is a seed treatment composition. In an embodiement, the present invention relates to a composition comprising the compound of formula I or II as above-defined, and one or more active ingredients, and optionally one or more customary formulation auxiliary.

The animal pest, i.e. the insects, arachnids and nematodes, the plant, seed, soil or water in which the plant is growing can be contacted with the present compound(s) of formula I or II or composition(s) thereof by any application method known in the art.

The compounds of formula I or II or the pesticidal compositions thereof may be used to protect growing plants and crops from attack or infestation by animal pests, especially insects, acaridae or arachnids by contacting the plant/crop with a pesticidally effective amount of compounds of formula I or II. The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers, seeds, or roots, of such plants, and in some cases even plant organs which are formed at a later point in time remain protected against these pests. The term "crop" refers both to growing and harvested crops.

Suitable target crops are, in particular, cereals, such as wheat, barley, rye, oats, rice, maize (fodder maize and sugar maize/sweet and field corn) or sorghum; beet, such as sugar or fodder beet; fruit, for example pomaceous fruit, stone fruit or soft fruit, such as apples, pears, plums, peaches, bananas, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, iceberg, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants, lawn, turf, fodder grass, and ornamentals, such as petunias, geranium/pelargoniums, pansies and impatiens.

In addition, the compound of formula I or II may also be used for the treatment of seeds or plants, which tolerate the action of herbicides or fungicides or insecticides owing to breeding, including genetic engineering methods.

Further, the compound of formula I or II may also be used for the treatment of genetically modified plant or seed containing one or more genes that confer resistance against insects, acarides, nematodes or fungi.

For example, crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

Furthermore, the compound of formula I or II can be used also for the treatment of plants and seeds, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

Moreover, animal pests may be controlled by contacting the target pest, its food supply, habitat, breeding ground or its locus with a pesticidally effective amount of compounds of formula I or II. As such, the application may be carried out before or after the infection of the locus, growing crops, or harvested crops by the pest.

The compounds of the invention can also be applied preventively to places at which occurrence of the pests is expected. The compounds of formula I or II may be also used to protect growing plants from attack or infestation by pests by contacting the plant with a pesticidally effective amount of compounds of formula I or II. As such, "contacting" includes both direct contact (applying the compounds/compositions directly on the pest and/or plant—typically to the seed, foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I or II are effective through both contact (e.g., via soil, glass, wall, bed net, carpet, plant parts or animal parts), and ingestion (bait, or plant part).

For use against ants, termites, wasps, flies, mosquitos, crickets, or cockroaches, compounds of formula I or II are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I or II as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250 Degrees C., dimethylformamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used. The compounds of formula I or II and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I or II and its respective compositions also comprise treating surfaces of huts and houses, air spraying and impregnation of curtains, tents, clothing items, bed nets, tsetse-fly trap or the like, Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), $N_1$N-diethylphenylacetamide (DEPA), 1-(3-cyclohexan-1-yl-carbonyl)-2-methylpiperine, (2-hydroxymethyl-cyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-i-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bed nets is done in general by dipping the textile material into emulsions or dispersions of the insecticide or spraying them onto the nets.

The compounds of formula I or II and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I or II are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Further areas of use of the compounds of formula I or II and compositions thereof according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, compounds of formula I or II and compositions thereof are suitable for control of ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., Raillietia spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

Compounds of formula I or II and compositions thereof are also suitable for protecting against insect infestation in the case of materials such as wood, textiles, plastics, adhesives, glues, paints, paper and card, leather, floor coverings and buildings.

In the case of soil treatment or of application to the pests dwelling place or nest, the quantity of active ingredient ranges from 0.0001 to 500 g per 100 $m^2$, preferably from 0.001 to 20 g per 100 $m^2$.

Customary application rates in the protection of materials are, for example, from 0.01 g to 1000 g of compound of formula I or II per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.001 weight % to 15 weight %, desirably from 0.001 weight % to 5% weight % of compound of formula I or II.

For use in spray compositions, the content of active ingredient is from 0.001 to 80 weight %, preferably from 0.01 to 50 weight % and most preferably from 0.01 to 15 weight %.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I or II are particularly useful for the protection of a seed, for example, from soil pests, and the resulting plant's roots, shoots and foliage against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of a seed, for example, from insects, in particular from soil insects, and of the seedlings' roots, shoots and foliage from insects, in particular from soil and foliar insects, said method comprising contacting, for example, the seeds before sowing and/or after pregermination with a compound of the general formula I or II or a salt thereof. Particularly preferred is a method, wherein the plant's roots, shoots and/or foliage are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

In another aspect, the present invention relates to a seed comprising a compound of formula I or II as above defined.

The present invention also comprises seeds coated with or containing a compound of formula I or II.

The term "coated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient.

Seed treatment comprises all suitable seed treatment techniques known in the art, such as seed dressing, seed coating, seed dusting, seed soaking and seed pelleting. The seed treatment application of the compound formula I or II can be carried out by any known methods, such as spraying or by dusting the seeds before sowing or during the sowing/planting of the seeds.

Compositions which are especially useful for seed treatment are e.g.:

A Soluble concentrates (SL, LS) D Emulsions (EW, EO, ES)

E Suspensions (SC, OD, FS)

F Water-dispersible granules and water-soluble granules (WG, SG)

G Water-dispersible powders and water-soluble powders (WP, SP, WS)

H Gel-Formulations (GF) I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. It may also be applied during the sowing of the seeds.

In a preferred embodiment a FS formulation is used for seed treatment. Typcially, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I or II for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed treatment formulations may additionally also comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 1 12, C.I. Solvent Red 1, pigment blue 15:4, pigment blue 15:3, pigment blue 15:2, pigment blue 15:1, pigment blue 80, pigment yellow 1, pigment yellow 13, pigment red 1 12, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds of formula I or II are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising (or treated with) a compound of the formula I or II, or an agriculturally useful salt of I, as defined herein. The amount of the compounds of the formula I or II or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

A material treated with a compound of formula I or II, therefore, refers to any material, such as for example, a seed, wood, net, In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The following Examples are given by way of illustration and not by way of limitation of the invention.

SYNTHESIS EXAMPLES

SE1: N-Ethyl-4-fluoro-1,2-benzisothiazol-3-amine 1,1-dioxide (P1.15)

Step 1: 3-Chloro-4-fluoro-1,2-benzisothiazole 1,1-dioxide
1.1 g of 4-fluoro-1,2-benzisothiazol-3(2H)-one 1,1-dioxide (EP291851 A2 19881123), 2 g of thionyl chloride and a catalytic amount of DMF in 6 ml of dioxane are heated under reflux for 18 hours. Then additional 2 g of thionyl chloride are added and the mixture is heated for 8 hours. The mixture is concentrated and 1.12 g of a crude solid is obtained.

Step 2: N-Ethyl-4-fluoro-1,2-benzisothiazol-3-amine 1,1-dioxide
120 mg of crude 3-chloro-4-fluoro-1,2-benzisothiazole 1,1-dioxide, obtained in step 1, is dissolved in 4 ml of dioxane and 0.15 ml of triethylamine is added. Then gaseous ethylamine is introduced. After stirring for 28 hours at room temperature the reaction mixture is poured into water. The aqueous phase is extracted three times with ethyl acetate. The combined organic phases are dried ($Na_2SO_4$), filtered and concentrated. Chromatography of the residue with n-heptane-acetone (9:1) affords 111 mg of N-Ethyl-4-fluoro-1,2-benzisothiazol-3-amine 1,1-dioxide as a beige solid (m.p. 236-238° C.).

SE2: 4-Fluoro-2-cyclopropylmethyl-1,2-benzisothiazol-3(2H)-imine 1,1-dioxide (P2.3)

100 mg of 2-cyano-3-fluoro-benzenesulfonyl chloride (EP33984 A1 19810819) is added to a solution of 0.85 ml of cyclopropylmethylamin in 3.5 ml of THF. After stirring for 3 hours at room temperature the reaction mixture is poured into water. The mixture is acidified with hydrochloric acid (~pH3) and extracted three times with methylenchloride. The combined organic phases are dried ($Na_2SO_4$), filtered and concentrated. Preparative HPLC affords 16 mg of 4-fluoro-2-cyclopropylmethyl-1,2-benzisothiazol-3(2H)-imine 1,1-dioxide as an orange solid (m.p. 90-93° C.).

Compounds in Table P1 and P2 can be made by methods described herein.

The following method is used for LC-MS analysis:

Method (Waters Alliance 2795 LC) with the following HPLC gradient conditions (Solvent A: 0.1% of formic acid in water/acetonitrile (9:1) and Solvent B: 0.1% of formic acid in acetonitrile)

| Time (minutes) | A (%) | B (%) | Flow rate (ml/min) |
|---|---|---|---|
| 0 | 90 | 10 | 1.7 |
| 2.5 | 0 | 100 | 1.7 |
| 2.8 | 0 | 100 | 1.7 |
| 2.9 | 90 | 10 | 1.7 |

Type of column: Waters Atlantis dc18; Column length: 20 mm; Internal diameter of column: 3 mm; Particle Size: 3 micron; Temperature: 40° C.

Table P1: Lists the compound of formula below which are prepared and characterised.

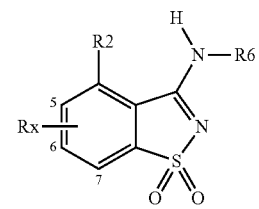

| Line | $R^2$ | $R^6$ | Rx | LC/MS RT (Min) | mass peak and/or m.p. |
|---|---|---|---|---|---|
| P1.1 | Cl | Methyl | H | 1.03 | $[M+H]^+$ = 231/233 m.p. > 250° C. |
| P1.2 | Cl | Ethyl | H | 1.26 | $[M+H]^+$ = 245/247 m.p. 209-211° C. |
| P1.3 | Cl | n-Propyl | H | 1.45 | $[M+H]^+$ = 259/261 m.p. 178-179° C. |
| P1.4 | Cl | Isopropyl | H | 1.48 | $[M+H]^+$ = 259/261 m.p. 158-159° C. |

-continued

| Line | R² | R⁶ | Rx | LC/MS RT (Min) | mass peak and/or m.p. |
|---|---|---|---|---|---|
| P1.5 | Cl | Cyclo-propyl | H | 1.28 | [M + H]⁺ = 2571/259 m.p. 211-213° C. |
| P1.6 | Cl |  | H | 1.46 | [M + H]⁺ = 342/344/346 m.p. 178-180° C. |
| P1.7 | Cl | 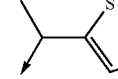 | H | 1.71 | [M + Na]⁺ = 349/351 m.p. 150-152° C. |
| P1.8 | Cl | 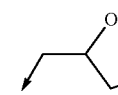 | H | 1.39 | [M + H]⁺ = 301/303 |
| P1.9 | Cl | 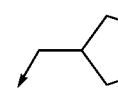 | H | 1.28 | [M + H]⁺ = 301/303 m.p. 150-152° C. |
| P1.10 | Cl | 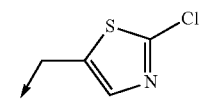 | H | 1.50 | [M + H]⁺ = 348/350/352 m.p. 231-233° C. |
| P1.11 | Cl | CN | H | 1.57 | [2M + H]⁺ = 483/485/487 |
| P1.12 | Cl | Allyl | H | 1.34 | [M + H]⁺ = 257/259 m.p. 147-148° C. |
| P1.13 | Cl | Propargyl | H | 1.20 | [M + H]⁺ = 255/257 m.p. 204-205° C. |
| P1.14 | F | Methyl | H | 0.81 | [M + H]⁺ = 215 m.p. 278-279° C. |
| P1.15 | F | Ethyl | H | 1.09 | [M + H]⁺ = 229 m.p. 236-238° C. |
| P1.16 | F | n-Propyl | H | 1.30 | [M + H]⁺ = 243 m.p. 181-183° C. |
| P1.17 | F | Cyclo-propyl | H | 1.57 | [M + H]⁺ = 241 m.p. 260-261° C. |
| P1.18 | F | Allyl | H | 1.16 | [M + H]⁺ = 241 m.p. 209-210° C. |
| P1.19 | F | Propargyl | H | 1.16 | [M + H]⁺ = 239 m.p. 256-257° C. |
| P1.20 | F |  | H | 1.37 | [M + H]⁺ = 326/328 m.p. 244-245° C. |
| P1.21 | F | 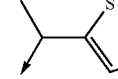 | H | 1.57 | [M + H]⁺ = 311 m.p. 198-199° C. |

Table P2: Lists the compound of formula below which are prepared and characterised.

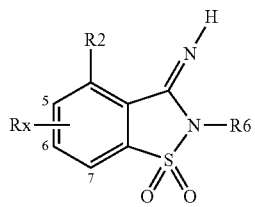

| Line | R² | R⁶ | Rx | LC/MS RT (Min) | mass peak and/or m.p. |
|---|---|---|---|---|---|
| P2.1 | Cl | n-Propyl | H | 1.59 | [M + H]⁺ = 259/261 m.p. 99-101° C. |
| P2.2 | F | n-Propyl | H |  | m.p. 100-102° C. |
| P2.3 | F |  | H |  | m.p. 90-93° C. |
| P2.4 | F | n-Butyl | H | 1.58 | [M − H]⁻ = 255 |

BIOLOGY EXAMPLES

B1: *Myzus persicae* (green peach aphid) (mixed population, sachet test)

Each well of a 24-well microtiter plate was filled with 0.6 ml 30% sucrose solution, containing 12.5 ppm of the test compounds. For producing the sachets, the wells were covered with streched parafilm and infested with a mixed population of *Myzus persicae*. 6 days after the infestation, samples were checked for mortality (feeding activity).

Compound P1.1 gives at least 80% control of *Myzus persicae*.

B2: *Myzus persicae* (green peach aphid) (mixed population, feeding/residual contact activity, preventive)

Sunflower leaf discs were placed on agar in a 24-well microtiter plate and sprayed with test solutions of 200 ppm. After drying, the leaf discs were infested with an aphid population of mixed ages. After an incubation period of 6 days, samples were checked for mortality and special effects (e.g. phytotoxicity).

Compounds P1.15 and P2.1 give at least 65% control of *Myzus persicae*.

B3: *Myzus persicae* (green peach aphid) (mixed population, systemic/feeding activity, curative)

Roots of pea seedlings, infested with an aphid population of mixed ages, were placed directly in the test solutions of 24 ppm. 6 days after introduction, samples were checked for mortality and special effects on the plant.

Compounds P1.1, P1.2, P1.3, P1.5, P1.6, P1.8, P1.12, P1.13, P1.14, P1.15, P1.16, P1.17, P1.18, P1.19, P2.2, P2.3 and P2.4 give at least 80% control of *Myzus persicae*.

The invention claimed is:
1. A compound of formula II:

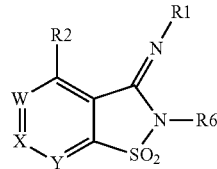

where:
W is C—R³;
X is C—R⁴;
Y is C—R⁵;
R1 is hydrogen;
R2 is halogen;
R³, R⁴ and R⁵, independently of each other, are H, halogen, cyano, nitro, C1-C6-alkyl, C1-C6-alkoxy, C1-C6-haloalkyl, C3-C8-cycloalkyl, C2-C6-alkenyl, C2-C6-alkynyl, OD or aryl; where D is C1-C6-alkyl, C1-C6-haloalkyl, C2-C6-alkenyl, C2-C6-alkynyl, C3-C8-cycloalkyl, or aryl; and where the aryl, whenever mentioned, independent of each other, may be unsubstituted, have one or more halogen atoms and/or carry 1, 2 or 3 substituents, independently of one another, selected from the group consisting of cyano, C1-C6-alkyl, C1-C6-haloalkyl, C1-C6-alkoxy and C1-C6-haloalkoxy; and
R6, for formula II, is CN, C3-C8-cycloalkyl, C3-C8-cycloalkyl-C1-C4-alkyl, which may have one or more halogen atoms on the alkyl group and/or cycloalkyl group, C2-C6-alkynyl, C2-C6-haloalkenyl, C2-C6-haloalkynyl, aryl-C1-C4-alkyl, heterocyclyl-C1-C4-alkyl or C3-C6-alkyl, wherein the C3-C6-alkyl radical is substituted with one or more halogen atoms and/or substituted with 1, 2 or 3 radicals, independently of one another, each selected from the group consisting of cyano, nitro, amino, OH, C1-C6-haloalkyl, C1-C6-alkoxy, C1-C6-haloalkoxy, C1-C6-alkylthio, C1-C6-alkylsulfinyl, C1-C6-alkylsulfonyl, C1-C6-haloalkoxy, C1-C6-haloalkylthio, (C1-C6-alkoxy)carbonyl, (C1-C6-alkyl)amino, and di-(C1-C6-alkyl)amino, the aryl group may be unsubstituted, have one or more halogen atoms and/or carry 1, 2 or 3 substituents, independently of one another, selected from the group consisting of C1-C6-alkyl, C1-C6-haloalkyl, C1-C6-alkoxy, C1-C6-haloalkoxy, cyano, and nitro; and the heterocyclyl group is a 4-7 membered saturated, partially unsaturated or aromatic heterocycle which may contain 1, 2, or 3 heteroatom and/or heteroatom group as ring members, independently of one another, selected from C(=O), O, S, and N and may be unsubstituted or substituted with one or two substituents selected from halogen, C1-C6-(halo)alkyl, and C1-C6-(halo)alkoxy;
and/or salts thereof.
2. The compound according to claim 1 wherein R³, R⁴ and R⁵, independently of each other, are selected from H, halogen, C1-C6-alkoxy and C1-C6-alkyl.
3. The compound according to claim 2 wherein R6, in formula II, is heterocyclyl-C1-C3-alkyl, wherein the heterocyclyl group is a saturated, partially unsaturated or aromatic 5 or 6 membered ring containing, as ring members, one or two heteroatoms selected, independently of one another, from N, O and S, which may be unsubstituted or substituted with one or two halogen substituents.
4. The compound according to claim 2 wherein R6 in formula II is a substituted C3-C6-alkyl.
5. The compound according to claim 1 wherein R⁵ is halogen.
6. The compound according to claim 1 wherein R2 is fluoro.
7. The compound according to claim 1 wherein R2 is chloro.
8. A composition comprising the compound of claim 1 and one or more formulation auxiliaries.
9. A composition comprising the compound of claim 1, and one or more active ingredients, and optionally one or more formulation auxiliaries.
10. A method for controlling a pest in crop protection or for protecting a seed, a plant, parts of a plant and/or plant organs that grow at a later point in time against pest damage which comprises applying a compound of claim 1 or a composition thereof to the pest, to the plant, to the seed, to the part of a plant and/or plant organ and/or the environment of each thereof.
11. A seed comprising a compound of claim 1.
12. A method for controlling a pest which comprises applying a compound as defined in claim 1 to the pest, material for protection and/or environment thereof.
13. The method according to claim 12 wherein the material is selected from a raw material, such as wood, textile, floor covering and building material.
14. The method according to claim 12 wherein the pest is controlled against damaging stored goods.
15. The method according to claim 12 wherein the pest is controlled in the hygiene sector, especially the protection of humans, domestic animals and productive livestock.
16. The compound according to claim 6 wherein R6, for formula II, is C3-C8-cycloalkyl, C3-C8-cycloalkyl-C1-C4-alkyl, which may have one or more halogen atoms on the alkyl group and/or cycloalkyl group, or C3-C6-alkyl, wherein the C3-C6-alkyl radical is substituted with one or more halogen atoms and/or substituted with 1, 2 or 3 radicals, independently of one another, each selected from the group consisting of cyano, nitro, amino, OH, C1-C6-haloalkyl, C1-C6-alkoxy, C1-C6-haloalkoxy, C1-C6-alkylthio, C1-C6-alkylsulfinyl, C1-C6-alkylsulfonyl, C1-C6-haloalkoxy, C1-C6-haloalkylthio, (C1-C6-alkoxy)carbonyl, (C1-C6-alkyl)amino, anddi-(C1-C6-alkyl)amino, the aryl group may be unsubstituted, have one or more halogen atoms and/or carry 1, 2 or 3 substituents, independently of one another, selected from the group consisting of C1-C6-alkyl, C1-C6-haloalkyl, C1-C6-alkoxy, C1-C6-haloalkoxy, cyano, and nitro; and the heterocyclyl group is a 4-7 membered saturated, partially unsaturated or aromatic heterocycle which may contain 1, 2, or 3 heteroatom and/or heteroatom group as ring members, independently of one another, selected from C(=O), O, S, and N and may be unsubstituted or substituted with one or two substituents selected from halogen, C1-C6-(halo)alkyl, and C1-C6-(halo)alkoxy.
17. The compound according to claim 2 wherein R6, for formula II, is C3-C8-cycloalkyl-C1-C4-alkyl, which may have one or more halogen atoms on the alkyl group and/or cycloalkyl group, or substituted C3-C6-alkyl.

* * * * *